United States Patent [19]

Drake

[11] 4,172,849
[45] Oct. 30, 1979

[54] CERIUM REGENERATION AID FOR RUTHENIUM HYDROGENATION CATALYST

[75] Inventor: Charles A. Drake, Bartlesville, Okla.

[73] Assignee: Phillips Petroleum Company, Bartlesville, Okla.

[21] Appl. No.: 954,158

[22] Filed: Oct. 24, 1978

[51] Int. Cl.$^2$ ............................................. C07C 85/12
[52] U.S. Cl. ............................... 260/583 P; 252/462; 260/583 K; 260/690
[58] Field of Search ............... 260/583 P, 583 K, 690; 252/462

[56] References Cited

U.S. PATENT DOCUMENTS

| | | | |
|---|---|---|---|
| 3,404,098 | 10/1968 | Stiles | 252/443 |
| 3,518,206 | 6/1970 | Sowards et al. | 252/446 |
| 3,679,773 | 7/1972 | Kovach et al. | 252/462 X |
| 3,794,588 | 2/1974 | Stiles | 252/462 |
| 3,880,929 | 4/1975 | Drake | 260/583 P |
| 3,896,173 | 7/1975 | Drake | 260/583 P |
| 4,053,515 | 10/1977 | Drake | 260/583 P |

FOREIGN PATENT DOCUMENTS

2131746 12/1971 Fed. Rep. of Germany ...... 260/583 K

*Primary Examiner*—Winston A. Douglas
*Assistant Examiner*—John Doll

[57] ABSTRACT

In a ruthenium hydrogenation catalyst cerium moderates loss in catalytic activity and the physical degradation of the catalyst. In one embodiment, upon repeated regenerations during the catalytic hydrogenation of branched chain olefinically unsaturated aliphatic dinitriles, a ruthenium-cerium/Al$_2$O$_3$ catalyst maintained a catalytic activity at higher levels through a series of hydrogenations and regenerations than did a catalyst containing only ruthenium.

10 Claims, No Drawings

CERIUM REGENERATION AID FOR RUTHENIUM HYDROGENATION CATALYST

This invention relates to catalytic hydrogenation. In one of its aspects it relates to the catalytic hydrogenation of branched chain olefinically unsaturated aliphatic dinitrile in the presence of a ruthenium catalyst having resistance to loss of activity and to physical degradation upon repeated use for hydrogenation and regeneration. In a more specific aspect of the invention it relates to a modified ruthenium catalyst suited for hydrogenation with repeated regenerations of the catalyst.

In one of its concepts the invention provides a method for the catalytic hydrogenation of branched chain olefinically unsaturated aliphatic dinitriles in the presence of a modified ruthenium catalyst, the catalyst having been modified by inclusion of cerium therein.

The catalytic hydrogenation of branched chain olefinically unsaturated aliphatic dinitriles in the presence of a ruthenium catalyst results in acceptable hydrogenation initially, but upon repeated hydrogenations and regenerations, the catalyst loses activity and undergoes physical degradation.

As illustrated by the data herein I have discovered that the presence of cerium in a ruthenium hydrogenation catalyst, as used for the hydrogenation of branched chain olefinically unsaturated aliphatic dinitriles, permits use of the catalyst upon repeated hydrogenations and regenerations with considerably less loss of activity and degradation than without the use of the cerium.

It is an object of this invention to provide a method for the hydrogenation of branched chain olefinically unsaturated aliphatic dinitriles. It is another object of this invention to provide a method for such hydrogenation in which the catalyst will have improved resistance to physical degradation. A further object of the invention is to provide a method for such hydrogenation in which the catalyst will retain considerably better its initial hydrogenation activity even after repeated hydrogenations and regenerations.

According to the present invention branched chain olefinically unsaturated dinitrile is hydrogenated in the presence of a catalyst containing both ruthenium and cerium. Also according to the invention and in a now preferred form thereof, the catalyst employed is a Ru-Ce/Al$_2$O$_3$ composition which can be variously prepared as one skilled in the art in possession of this disclosure, having studied the same, will understand.

The branched chain unsaturated aliphatic dinitriles which can be advantageously and efficiently hydrogenated in accordance with the process of this invention include unsaturated dinitriles of the formula

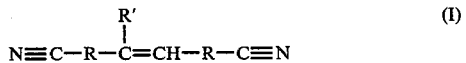
 (I)

wherein each R is independently selected from the group consisting of an alkylene radical and an alkylidene radical, and R' is an alkyl radical. Each R will generally have from 1 to 15 carbon atoms, preferably from 1 to 6 and more preferably from 1 to 3 carbon atoms. R' will generally have from 1 to 15 carbon atoms, preferably from 1 to 6 carbon atoms, and more preferably from 1 to 3 carbon atoms. In general, the unsaturated dinitrile reactant of formula (I) will contain from 7 to 30 carbon atoms, preferably from 8 to 16 carbon atoms, and more preferably from 9 to 12 carbon atoms.

Representative of unsaturated reactant species of formula (I) include such compounds as 3-methyl-3-hexenedinitrile, 3-ethyl-3-hexenedinitrile, 5-methyl-4-nonenedinitrile, 5-ethyl-4-decenedinitrile, 7-methyl-6-tridecenedinitrile, 7-methyl-6-pentadecenedinitrile, 12-methyl-12-tetracosenedinitrile, 10-hexyl-9-tetracosenedinitrile, 2,3-dimethyl-3-hexenedinitrile, 2,4,6-trimethyl-3-heptenedinitrile, 4-ethyl-6,7-dimethyl-3-octenedinitrile, 2,4,6-triethyl-3-octenedinitrile, 2-ethyl-4,6-dipropyl-3-octenedinitrile, 2-methyl-4,6,8,10-tetrapropyl-3-dodecenedinitrile, 2,4,7,9,11,13,15-heptaethyl-6-hexadecenedinitrile, and mixtures thereof.

Other unsaturated dinitrile reactants can be present and effectively hydrogenated during the hydrogenation of the unsaturated dinitriles of formula (I). Thus, in addition to the unsaturated dinitrile reactants of formula (I), the dinitrile feedstock can contain one or more unsaturated dinitrile reactants of the formula:

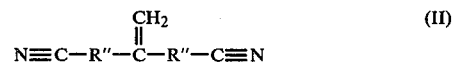
 (II)

wherein each R" is independently selected from the group consisting of an alkylene radical and an alkylidene radical. In general, each R" will have from 1 to 15 carbon atoms, preferably from 1 to 7 carbon atoms, and more preferably from 1 to 4 carbon atoms. The dinitriles of formula (II) will generally contain from 6 to 30 carbon atoms, preferably from 8 to 16 carbon atoms, and more preferably from 9 to 12 carbon atoms. Representative unsaturated dinitrile reactants of formula (II) include such compounds as 3-methylenehexanedinitrile, 4-methyleneheptanedinitrile, 5-methylenenonanedinitrile, 6-methyleneundecanedinitrile, 7-methylenetridecanedinitrile, 8-methylenepentadecanedinitrile, 12-methylenetetracosanedinitrile, 15-methylenenonacosanedinitrile, 2-methyl-3-methylenepentanedinitrile, 2,4-dimethyl-3-methylenepentanedinitrile, 2-methyl-4-methyleneoctanedinitrile, 2-methyl-7-ethyl-4-methyleneoctanedinitrile, 2,4,8-trimethyl-6-methylenedodecanedinitrile, 2,4,8,10-tetrapropyl-6-methylenedodecanedinitrile, 2,26-dimethyl-14-methyleneheptacosanedinitrile, and mixtures thereof.

Unsaturated dinitriles having a structure other than that of formulas (I) and (II) can be present during the hydrogenation reaction, if desired. Similarly, other compounds which may be found in the feed source of the dinitriles of formulas (I) and (II) can be present so long as such additional compounds do not significantly adversely affect the hydrogenation of the dinitriles of formulas (I) and (II). Where other dinitriles are present in the feedstock, the dinitriles of formula (I) will generally constitute at least 0.1 weight percent of the total dinitriles. The significant advantages of the invention increase with increasing concentration of the dinitriles of formula (I) in the feedstock. Thus, the process of the invention is even more advantageous for concentrations of the dinitriles of formula (I) in the feedstock of at least 5 weight percent. The invention is considered to be particularly desirable for dinitrile feestocks having a concentration of the dinitriles of formula (I) of at least 10 weight percent.

A presently preferred branched-chain unsaturated aliphatic dinitrile feedstock for employment in the practice of this invention is the dinitrile reaction product mixture obtained by the reaction of isobutylene and acrylonitrile as known in the art. This dinitrile reaction product mixture generally comprises 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile. The first four named compounds in this mixture are of the type of formula (I), while the last three named compounds in this mixture are of the type formula (II). The weight ratio of the dinitriles of formula (I) to the dinitriles of formula (II) in this mixture is generally in the range of from about 10:1 to about 1:10.

In the practice of this invention, the catalytic hydrogenation of the unsaturated dinitrile reactant of formula (I) results primarily in the formation of substantially saturated diamine reaction products having the formula

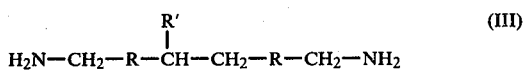

wherein R and R' are as previously defined. The catalytic hydrogenation of an unsaturated dinitrile reactant of formula (II) results primarily in the formation of substantially saturated diamine reaction products having the formula

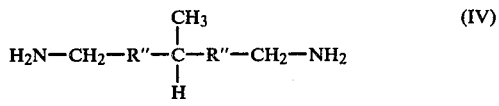

wherein R'' is as previously defined.

The catalysts that are considered to be suitable for employment, in a modified form according to the invention, are those catalysts containing elemental ruthenium or compounds of ruthenium which are reducible by hydrogen to finely divided elemental ruthenium and mixtures thereof. Suitable reducible compounds include the oxides, halides, nitrates, oxalates, acetates, carbonates, acetylacetonates, hydroxides, and the like, and mixtures thereof. Specific examples include ruthenium dioxide, ruthenium tetraoxide, ruthenium tribromide, ruthenium trichloride, ruthenium trinitrate, ruthenium triacetate, ruthenium(III) carbonate, ruthenium(III) acetylacetonate, ruthenium(III) hydroxide, and the like, and mixtures thereof.

For the purpose of maintaining reasonable reaction rates under economically attractive catalyst reaction kinetics, it is generally preferred that the weight ratio of the ruthenium component to the unsaturated dinitrile reactants be maintained within a range of about 0.01:100 to about 30:100, and, preferably in the range of about 0.1:100 to about 20:100.

The regeneration aid, i.e., the cerium, improves the catalyst regeneration, e.g., by helping to maintain a high catalyst activity and/or by improving the catalyst's physical stability during regenerations. The regeneration aid which can be employed according to the process of this invention can be selected from elemental cerium, compounds of cerium, and mixtures thereof. Suitable compounds of cerium include cerium(III) acetate, cerium(III) benzoate, cerium(III) bromide, cerium(III) chloride, cerium(III) carbonate, cerium(III) nitrate, cerium(IV) hydroxide, cerium(IV) oxide, and the like and mixtures thereof. The presently preferred compounds of cerium are cerium(III) acetate, cerium(III) chloride, and cerium(III) nitrate.

The amount of the cerium regeneration aid can be any amount that provides an improvement in regenerability to the catalyst. The optimum amount can be determined by routine tests. In general, the amount of cerium expressed as a Ce:Ru weight ratio will range from about 1:100 to about 200:100 and for economic reasons will preferably range from about 10:100 to about 100:100.

In the practice of this invention, it is often desirable to employ catalytic amounts of elemental ruthenium, reducible compounds of ruthenium, or mixtures thereof and a cerium regeneration aid supported by a solid catalyst carrier which does not deleteriously affect the catalytic hydrogenation process of this invention. Such supports include, for example, carbon, kieselguhr, silica, alumina, silica-alumina, calcium carbonate, barium carbonate, asbestos, pumice, clays, and the like, and mixtures thereof. The support can be in the form of spheres, pills, extrudates, granules, and the like, and mixtures thereof.

The ruthenium catalyst components and the cerium regeneration aid can be added to the support by any of the methods well known in the art. For example, the supported catalyst can be prepared by dry mixing the components or by impregnating the support with a solution or a slurry of elemental cerium or a cerium compound and elemental ruthenium or reducible compound thereof. The cerium and ruthenium components can be added to the support together or separately in any order. When a cerium compound is deposited on a support before the ruthenium component, a calcination of the cerium impregnated support can be conducted, if desired, under any suitable conditions. In general, the calcination is conducted at a temperature in the range of about 230° C. to about 500° C. for a period of time in the range of about 0.5 hour to about 10 hours. The supported catalyst can be pretreated with hydrogen to reduce the compounds, or such reduction can be achieved in the hydrogenation reactor. When a support is employed in a batch process, the elemental ruthenium content will generally be in the range of about 0.5 to about 50 weight percent, preferably in the range of about 1 to about 10 weight percent, based on the weight of the support. For a continuous process, the elemental ruthenium content will generally be in the range of about 0.05 to about 50 weight percent, preferably in the range of about 0.1 to about 10 weight percent, based on the weight of the support. Specific examples of suitable catalysts include 2 weight percent ruthenium-1 weight percent cerium on alumina, 4 weight percent ruthenium-2 weight percent cerium on alumina, 2 weight percent ruthenium-1 weight percent cerium on silica, and 3 weight percent ruthenium-2 weight percent cerium on alumina.

Any catalytic hydrogenation temperature can be employed which provides the desired degree of catalytic efficiency in the hydrogenation of the branched-chain unsaturated aliphatic dinitrile containing feedstock. This temperature can be determined by routine tests. The hydrogenation temperature will generally be within the range of from about 30° to about 250° C. and preferably will be in the range of from about 70° to about 200° C.

The catalytic hydrogenation of the branched-chain unsaturated aliphatic dinitriles can be carried out at any hydrogen pressure, determined by routine test, at which both the olefinic unsaturation and the nitrile groups are reduced. Generally, suitable hydrogen pressures are within the range of from about 100 to about 5000 psig, but lower or even higher hydrogen pressures can be employed. Preferably, due to economic considerations, hydrogen pressures within the range of about 500 to about 3000 psig are employed. Higher hydrogen pressures may be desirable at lower reaction temperatures in order to achieve complete reduction within a reasonable reaction time.

Any time interval determined by a routine test suited for the catalytic hydrogenation of branched-chain unsaturated aliphatic dinitriles can be employed in the practice of this invention. However, time intervals economically attractive to the process are generally within the range of from about 15 minutes to about 10 hours for a batch hydrogenation process. The catalytic hydrogenation of unsaturated dinitriles in accordance with the process of this invention can be carried out as a continuous process at any suitable, experimentally determined, liquid hourly space velocity (LHSV). However, the liquid hourly space velocity rates will generally be within the range of from about 0.1 to about 10, more preferably from about 0.5 to about 7, volumes of unsaturated dinitrile reactant plus diluent per volume of catalyst (including the volume of the catalyst support) per hour.

While any suitable diluent can be employed in the process of this invention, the diluent will generally be selected from the class consisting of unsubstituted alkanols containing from 1 to 12 carbon atoms per molecule, unsubstituted acyclic and unsubstituted cyclic ethers having from 4 to 12 carbon atoms per molecule, and saturated hydrocarbons having 4 to 12 carbon atoms per molecule, and mixtures thereof. The term "unsubstituted" signifies that there are no substituents other than hydrocarbyl radicals. Examples of alkanol diluents include methanol, ethanol, 2-propanol, 2-methyl-2-propanol, 2-methyl-2-butanol, 2-butanol, 1-hexanol, 3-ethyl-3-hexanol, 2,4-dimethyl-2-pentanol, 2-decanol, 1-dodecanol, 2,3-dimethyl-3-pentanol, 3-ethyl-3-pentanol, 3,7-dimethyl-3-octanol, and the like, and mixtures thereof. The unsubstituted tertiary alkanols having at least 4 carbon atoms per molecule are the more preferred alkanol diluents. Examples of alkanes and cycloalkanes include butane, pentane, hexane, decane, dodecane, cyclobutane, cyclopentane, cyclohexane, cyclodecane, cyclododecane, 2-methylbutane, methylcyclopentane, 2,2,4-trimethylpentane, and mixtures thereof. Examples of ethers include 1,3-dioxane, 1,4-dioxane, tetrahydrofuran, 4,4-dimethyl-1,3-dioxane, and mixtures thereof. To facilitate handling of the reaction mixtures, the weight ratio of the unsaturated dinitrile reactants to diluent charged to the reaction zone is generally within the weight ratio range of about 0.001:100 to about 50:100, and is preferably in the range of about 0.1:100 to about 25:100.

A secondary amine formation suppressant, preferably ammonia, is employed in the process of this invention as a means of suppressing undesirable side reactions such as the formation of secondary and tertiary amines. Any amount of secondary amine formation suppressant can be employed which is effective in deterring or reducing undesirable side reactions. In general, the mole ratio of secondary amine formation suppressant to cyano group (there being two cyano groups in each unsaturated dinitrile) will be in the range of about 1:1 to about 25:1, and preferably will be in the range of about 7:1 to about 15:1.

Recovery of the desired end product, the branched-chain saturated aliphatic diamines, as well as any resulting reaction byproducts, any unconsumed reactants, ammonia, hydrogen, and/or diluents can be carried out by any conventional separation means. In general, at the conclusion of the catalytic hydrogenation in a batch process, the reaction effluent is cooled and depressurized with the recovery, if desired, of ammonia, or diluent which is vented from the reaction effluent during the depressurization operation. The ammonia or diluent can be returned or recycled to the hydrogenation zone if desired. The reaction products can be separated from the catalyst by conventional filtration means. The filtrate containing the saturated diamines can be conveniently separated from any reaction byproducts or any diluent remaining in the filtrate by a conventional fractional distillation. In a continuous hydrogenation reaction, the reaction effluent can be treated by conventional distillation techniques to remove the diluent, ammonia, products, and any byproducts. The recovered diluent and ammonia can be recycled to the hydrogenation zone if desired.

The saturated diamine products of this invention can be utilized in the preparation of polymeric materials. Of particular value are the polyamides formed with terephthalic acid. These terephthalamide polymers have been found to be of considerable value in the form of fibers and engineering plastics.

In the examples that follow, the hydrogenation substrate which is undergoing hydrogenation is an olefinically unsaturated dinitrile mixture prepared from isobutylene and acrylonitrile. The mixture contained approximately 52 weight % 5-methylenenonanedinitrile, approximately 35 weight % 5-methyl-4-nonenedinitrile, approximately 12 weight % of the combination of 2,4-dimethyl-4-octenedinitrile, 2-methyl-4-methyleneoctanedinitrile, and 2,4-dimethyl-3-octenedinitrile, and approximately 1 weight % of the combination of 2,6-dimethyl-4-methyleneheptanedinitrile and 2,4,6-trimethyl-3-heptenedinitrile. For convenience, the above described mixture will be described as diadduct in the examples below.

In each of the runs described in the examples below, a 0.5" (12.7 mm) diameter×20" (508 mm) length continuous reactor fitted with a steam heating system and a temperature recorder and containing about 20 ml of the supported catalyst was utilized. The reactor was flushed with nitrogen, flushed with hydrogen at a rate of 1 liter/minute, and heated to 140° C. A mixture containing diadduct, t-butyl alcohol, and ammonia in a weight ratio of 1/8/1 was fed to the reactor at a LHSV of about 6. Reactor conditions during the hydrogenations runs were 1500 psig (10.3 MPa) pressure, 140° C., and 1 liter/minute hydrogen flow.

Samples were collected from the reactor effluent after 4 hours of run time and after 19 hours of run time and were analyzed for reaction product composition by vapor phase chromatography after removal of the t-butyl alcohol and ammonia under reduced pressure.

All catalyst regenerations involved removing the supported catalyst from the above described reactor and charging the catalyst to an electrically heated reactor of the same dimensions as the above described reactor. The catalyst was first heated to 350° C. for 3 hours while nitrogen was passed over the catalyst at about 0.7 liters/minute and then was heated at 350° C. for 3 hours while a mixture of nitrogen at about 0.7 liters/minute and air at about 0.07 liters/minute was passed over the catalyst. The regenerated catalyst was allowed to cool to room temperature overnight, was reduced in the presence of hydrogen at about 400° C. for 3 hours, and was then charged to the steam heated reactor for another hydrogenation run.

The catalyst utilized in Example I was a 2 weight % ruthenium on alumina (Ru/Al$_2$O$_3$) catalyst prepared by impregnating a commercial 8 to 14 mesh granular γ-alumina with ruthenium chloride from an aqueous solution in a rotary evaporator and reducing the impregnated support in the presence of hydrogen at 400° C. for 3 hours.

The catalyst utilized in Example II was a 2 weight % ruthenium, 1 weight % cerium on alumina (Ru-Ce/Al$_2$O$_3$) catalyst prepared by impregnating a commercial 8 to 14 mesh granular γ-alumina with cerium acetate from methanol in a rotary evaporator, calcining at 350° C. for 3 hours in air, cooling to about room temperature, impregnating the cerium impregnated support with ruthenium chloride from methanol with a rotary evaporator, and reducing at 400° C. for 3 hours in the presence of hydrogen. The percentages used for the catalysts are based on the weight of the support.

EXAMPLE I

A series of control hydrogenation runs was carried out in which diadduct was hydrogenated to a mixture of saturated diamines in the presence of a Ru/Al$_2$O$_3$ catalyst. Run 1 utilized a fresh catalyst and the used catalyst recovered at the end of run 1 was regenerated and utilized in run 2. The used catalyst from run 2 was regenerated and utilized in run 3 and so forth for a total of 7 runs. The results of these runs are presented in Table I.

Table I

| Run[a] No. | Saturated Diamines,[b] Weight % | |
|---|---|---|
| | 4 hours | 19 hours |
| 1 | 95 | 98 |
| 2 | 94 | 91 |
| 3 | 90 | 79 |
| 4 | 86 | 81 |
| 5 | 80 | 54 |
| 6 | 82 | 72 |
| 7[c] | 74 | 48 |

[a]Catalyst = Ru/Al$_2$O$_3$ containing 2 weight % Ru based on the weight of the support.
[b]Weight % saturated diamines in the reaction product at the indicated number of hours in the run. The % is based on the total product weight following removal of diluent and ammonia.
[c]Catalyst powdered by end of run.

The results presented in Table I show that the catalytic activity of the Ru/Al$_2$O$_3$ catalyst (as indicated by the levels of saturated diamines present in the product) decreases substantially after a series of regenerations. In addition, by the conclusion of run 7, the catalyst degraded to a powder which was unacceptable for further use.

EXAMPLE II

A series of runs was carried out according to this invention utilizing a Ru-Ce/Al$_2$O$_3$ catalyst for the hydrogenation of diadduct to a mixture of saturated diamines. Run 8 utilized a fresh catalyst and the used catalyst from run 8 was regenerated and utilized in run 9. The used catalyst recovered from run 9 was regenerated and utilized in run 10 and so forth for a total of 9 runs. The results of these runs are presented in Table II.

Table II

| Run[a] No. | Saturated Diamines,[b] Weight % | |
|---|---|---|
| | 4 hours | 19 hours |
| 8 | 94 | 92 |
| 9 | 95 | 90 |
| 10 | 93 | 92 |
| 11 | 88 | 80 |
| 12 | 88 | 83 |
| 13 | 88 | 73 |
| 14 | 95 | 82 |
| 15 | 87 | 62 |
| 16 | 74 | 65 |

[a]Catalyst = Ru-Ce/Al$_2$O$_3$ containing 2 weight % Ru and 1 weight % Ce based on the support weight.
[b]See footnote (b) of Table I.

The results presented in Table II show that the presence of cerium with the ruthenium catalyst helps maintain the catalytic activity at a higher level through a series of hydrogenations and regenerations than the ruthenium catalyst in Example I. Since the levels of saturated diamines in run 8 are slightly lower than in run 1, it appears that the presence of cerium does not have an activating or promoting effect on the Ru catalyst. The catalyst at the conclusion of run 16 showed no signs of physical degradation.

A comparison of the results of Example II with the results of Example I shows that the use of the cerium regeneration aid of this invention with a ruthenium catalyst results in a higher catalytic activity through a series of hydrogenations and regenerations without physical degradation than a ruthenium catalyst without a cerium regeneration aid.

Reasonable variation and modification are possible within the scope of the foregoing disclosure and the appended claims to the invention the essence of which is that cerium has been found to considerably improve or modify a ruthenium hydrogenation catalyst employed in the catalytic hydrogenation of branched-chain olefinically unsaturated aliphatic dinitriles improving not only loss of activity but also considerably avoiding physical degradation of the catalyst through repeated hydrogenations and regenerations.

I claim:

1. The process of hydrogenating of a branched-chain olefinically unsaturated aliphatic dinitrile by contacting said dinitrile with a ruthenium-cerium catalyst upon a suitable support under suitable hydrogenating conditions.

2. The process according to claim 1 wherein the branched-chain unsaturated aliphatic dinitrile is represented by the formula

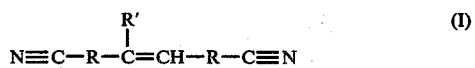

in which each R is independently selected from an alkylene radical and an alkylidene radical and R' is an alkyl radical.

3. The process according to claim 2 wherein each R and each R' contains from 1 to 15 carbon atoms and the dinitrile contains from 7 to 30 carbon atoms.

4. A process according to claim 1 wherein the catalyst is supported on an alumina catalyst support.

5. A process according to claim 4 wherein gamma-alumina is impregnated with cerium compound, calcined, and thus prepared catalyst base is impregnated with ruthenium compound and then reduced.

6. A process according to claim 1 wherein the catalyst includes elemental ruthenium in the range of from about 0.05 to about 50 weight % based on the weight of the support and from about 1 to about 200 weight % cerium based on the amount of elemental ruthenium.

7. A process according to claim 6 wherein the elemental ruthenium is in the range of from about 0.05 to about 50 weight % and a continuous hydrogenation is conducted.

8. A process according to claim 6 wherein the elemental ruthenium is in the range of from about 0.5 to about 50 weight % and a batch hydrogenation is conducted.

9. The hydrogenation of claim 1 wherein the compound hydrogenated is comprised within a mixture containing at least one of the following: 5-methylenenonanedinitrile, 5-methyl-4-nonenedinitrile, 2,4-dimethyl-4-octenedinitrile, 2-methyl-4-methyleneoctanedinitrile, 2,4-dimethyl-3-octenedinitrile, 2,6-dimethyl-4-methyleneheptanedinitrile, and 2,4,6-trimethyl-3-heptenedinitrile.

10. A process according to claim 9 wherein the hydrogenation is effected upon a mixture containing a substantial portion of each of said unsaturated dinitriles.

* * * * *